United States Patent
Adamson et al.

(10) Patent No.: US 9,598,666 B2
(45) Date of Patent: Mar. 21, 2017

(54) FLUID DISTRIBUTION IN A SAMPLE EXPOSURE DEVICE

(71) Applicant: British American Tobacco (Investments) Limited, London (GB)

(72) Inventors: Jason Adamson, London (GB); Marianna Gaca, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 0 days.

(21) Appl. No.: 14/355,393

(22) PCT Filed: Oct. 29, 2012

(86) PCT No.: PCT/EP2012/071401
§ 371 (c)(1),
(2) Date: Apr. 30, 2014

(87) PCT Pub. No.: WO2013/064466
PCT Pub. Date: May 10, 2013

(65) Prior Publication Data
US 2014/0295546 A1    Oct. 2, 2014

(30) Foreign Application Priority Data
Oct. 31, 2011  (GB) .................................. 1118774.7

(51) Int. Cl.
*C12M 1/00*  (2006.01)
*B01L 1/02*  (2006.01)
(Continued)

(52) U.S. Cl.
CPC ............. *C12M 23/40* (2013.01); *B01L 1/025* (2013.01); *C12M 29/00* (2013.01);
(Continued)

(58) Field of Classification Search
CPC ............... B01L 3/5025; B01L 3/50255; B01L 3/50853; B01L 1/02; B01L 1/025; B01L 2200/0642
See application file for complete search history.

(56) References Cited

U.S. PATENT DOCUMENTS 4,461,328 A  *  7/1984  Kenney ............................ 141/67
4,493,815 A  *  1/1985  Fernwood et al. ............ 422/535
(Continued)

FOREIGN PATENT DOCUMENTS

CN      201560188 U     8/2010
DE        3407458 A1    9/1984
(Continued)

OTHER PUBLICATIONS

Wieczorek, R. et al., "Validation of a new smoking machine for the exposure of 96 well cell culture plates to 'native' cigarette mainstream smoke aerosol. Course of action and some in vitro toxicological data", CORESTA Meet. Smoke Sci.-Prod. Techno Groups, Stratford-upon-Afon, 2005, abstr. SSPT 24.

(Continued)

*Primary Examiner* — Jill Warden
*Assistant Examiner* — Matthew Krcha
(74) *Attorney, Agent, or Firm* — Cantor Colburn LLP (57) ABSTRACT

The invention relates to fluid distribution in an exposure device. The exposure device, in some examples, is a device for exposing living cell cultures or cellular tissues to a fluid such as cigarette smoke, air and/or other gases or gas mixtures, for use in studies of the effects on the cell cultures or tissues of their exposure to the fluid. A fluid distribution member is described for distributing the fluid in the exposure device, the member including a plurality of apertures in a surface arranged such that, when the distribution member is fitted to the fluid exposure device, the distribution member (Continued)

receives fluid applied to the surface of the member and distributes the fluid, via the apertures, to samples to be exposed to the fluid in the exposure device.

9 Claims, 7 Drawing Sheets (51) Int. Cl.
*B01L 3/00* (2006.01)
*B01L 5/00* (2006.01)

(52) U.S. Cl.
CPC .............. *B01L 3/50853* (2013.01); *B01L 5/00* (2013.01); *B01L 2200/023* (2013.01); *B01L 2200/025* (2013.01); *B01L 2200/026* (2013.01); *B01L 2300/041* (2013.01); *B01L 2300/047* (2013.01); *B01L 2300/048* (2013.01); *B01L 2300/0609* (2013.01); *B01L 2300/0829* (2013.01); *B01L 2300/0864* (2013.01); *B01L 2400/086* (2013.01)

(56) References Cited

U.S. PATENT DOCUMENTS

| 4,590,042 | A | * | 5/1986 | Drage | H01J 37/3244 156/345.34 |
|---|---|---|---|---|---|
| 4,792,378 | A | | 12/1988 | Rose et al. | |
| 5,585,275 | A | * | 12/1996 | Hudson | B01D 61/18 422/129 |
| 6,326,121 | B1 | * | 12/2001 | Takahashi | B41J 2/4753 347/192 |
| 7,662,565 | B2 | | 2/2010 | Albino et al. | |
| 7,727,715 | B2 | | 6/2010 | Jorgensen et al. | |
| 2003/0161763 | A1 | * | 8/2003 | Erden et al. | .............. 422/99 |
| 2004/0168694 | A1 | | 9/2004 | Fukano et al. | |
| 2006/0099706 | A1 | | 5/2006 | Massey et al. | |
| 2006/0191893 | A1 | * | 8/2006 | Weinfield et al. | .............. 219/428 |
| 2007/0264164 | A1 | * | 11/2007 | Hochstrasser et al. | ....... 422/102 |
| 2008/0052789 | A1 | | 2/2008 | Jorgensen et al. | |
| 2008/0227088 | A1 | | 9/2008 | Albino et al. | |
| 2010/0028986 | A1 | | 2/2010 | Hanafusa | |
| 2010/0206317 | A1 | | 8/2010 | Albino et al. | |

FOREIGN PATENT DOCUMENTS

| DE | 19526533 A1 | | 1/1997 |
| JP | 2000058294 A | * | 2/2000 |
| JP | 2004222533 A | | 8/2004 |
| WO | 03100417 A1 | | 12/2003 |

OTHER PUBLICATIONS

Scian, Mariano J. et al., "Characterization of a Whole Smoke In Vitro Exposure System (Burghart Mimic Smoker-01)", Inhalation Toxicology, vol. 21, pp. 234-243, 2009.

International Search Report and Written Opinion, mailed Feb. 7, 2013 for PCT/EP2012/071401, filed Oct. 29, 2012.

Written Opinion of the International Preliminary Examining Authority, mailed Nov. 15, 2013, for PCT/EP2012/071401, filed Oct. 29, 2012.

International Preliminary Report on Patentability, mailed Feb. 12, 2014, for PCT/EP2012/071401, filed Oct. 29, 2012.

* cited by examiner

FLUID DISTRIBUTION IN A SAMPLE EXPOSURE DEVICE

CLAIM FOR PRIORITY

This application is the National Stage of International Application No. PCT/EP2012/071401, filed Oct. 29, 2012, which in turn claims priority to and benefit of British Patent Application No. GB1118774.7, filed Oct. 31, 2011. The entire contents of the aforementioned applications are herein expressly incorporated by reference.

The invention relates to fluid distribution in an exposure device. The exposure device, in some examples, is a device for exposing living cell cultures or cellular tissues to a fluid such as cigarette smoke, air and/or other gases or gas mixtures, for use in studies of the effects on the cell cultures or tissues of their exposure to the fluid.

Various exposure devices are known for the delivery of gaseous matter to living cell cultures. Known devices facilitate the delivery of smoke and/or other fluids to cell culture chambers. The cell culture chambers can be used to hold a substrate or membrane containing the living cell cultures, and may or may not be supplied with nutrient medium.

Certain known exposure devices involve controlling the introduction of smoke individually into specific cell culture chambers, resulting in relatively complex and costly devices. The device described in International Patent Publication WO03/100417 addresses this issue by providing a single chamber into which smoke is directed, via a fluid dispersing means.

According to embodiments of the invention from a first aspect, there is provided a fluid distribution member for distributing a fluid in a fluid exposure device, the distribution member comprising a plurality of apertures in a surface of the member arranged such that, when the distribution member is fitted to the fluid exposure device, the distribution member receives fluid applied to the surface of the member and distributes the fluid, via the apertures, to samples to be exposed to the fluid in the exposure device.

The samples can be disposed in a plurality of sample chambers within the fluid exposure device and the apertures can be arranged, in use, so as to distribute the fluid to each of the plurality of sample chambers in the fluid exposure device.

The apertures can be provided in the form of a plurality of elongate slots or sets of slots extending in parallel across the distribution member. The slots can be arranged in accordance with an arrangement of samples to be exposed to the fluid in the fluid exposure device. The arrangement of samples can comprise an arrangement in a microtiter well format. The fluid distribution member can comprise between 2 and 30 slots or sets of one or more slots.

The fluid distribution member can comprise a side wall extending perpendicularly to the surface and circumscribing the surface.

The fluid distribution member can comprise a fluid exposure device connection part, for use in releasably connecting the member to the fluid exposure device. The fluid exposure device connection part can be arranged for use in connecting the member to the fluid exposure device in a limited number of orientations.

According to embodiments of the invention from a second aspect there is provided a connecting member for connecting a fluid distribution member to a fluid exposure device, the connecting member configured to releasably connect a plurality of fluid distribution members individually to the fluid exposure device.

The connecting member can be further configured to releasably connect the plurality of fluid distribution members individually to the fluid exposure device in a limited number of orientations with respect to the fluid exposure device.

The connecting member can be configured to releasably connect a plurality of fluid distribution members individually to a fluid exposure device.

The connecting member can further comprise an inlet for receiving fluid to be distributed by a fluid distribution member when connected by the connecting member to the fluid exposure device and one or more channels for supplying the fluid from the inlet to a surface of the fluid distribution member.

According to embodiments of the invention from a third aspect, there is provided a fluid exposure device for exposing samples to a fluid, the device arranged to receive a fluid distribution member as described herein.

The fluid exposure device can further comprise a connecting member as described herein.

The fluid exposure device can further comprise a fluid distribution member as described herein, wherein the device is arranged to provide the fluid to the surface of the member such that the distribution member distributes the fluid, via the apertures, to the samples.

The fluid exposure device can further comprise a cavity for receiving a plurality of sample chambers, the device being configured to provide substantially contemporaneous and uniform fluid exposure to each of the sample chambers.

The fluid can comprise at least one selected from single gases or mixtures of gases, combustion smoke, cigarette smoke, air, exhaust gases, cosmetic and pharmaceutical aerosols, other aerosolised consumer goods, pesticides, herbicides and engineered nanoparticles.

According to embodiments of the invention from a fourth aspect, there is provided a fluid exposure kit comprising a plurality of fluid distribution members, each as described herein, a connecting member as described herein and a fluid exposure device as described herein.

According to embodiments of the invention from a fifth aspect, there is provided a method of exposing samples to a fluid in a fluid exposure device, the method comprising providing a fluid to a surface of a fluid distribution member, the surface comprising a plurality of apertures, such that the fluid is distributed, via the apertures, to samples to be exposed to the fluid in the exposure device.

The exposure device used in the method can comprise a part of the fluid exposure kit described herein, and the method can further comprise selecting a particular fluid distribution member from the plurality of fluid distribution members according to an arrangement of samples to be exposed in the fluid exposure device and connecting the selected fluid distribution member to the fluid exposure device using the connecting member.

In order that the invention may be more fully understood and readily carried into effect, reference will now be made, by way of example, to the following drawings in which.

Figure 1A:
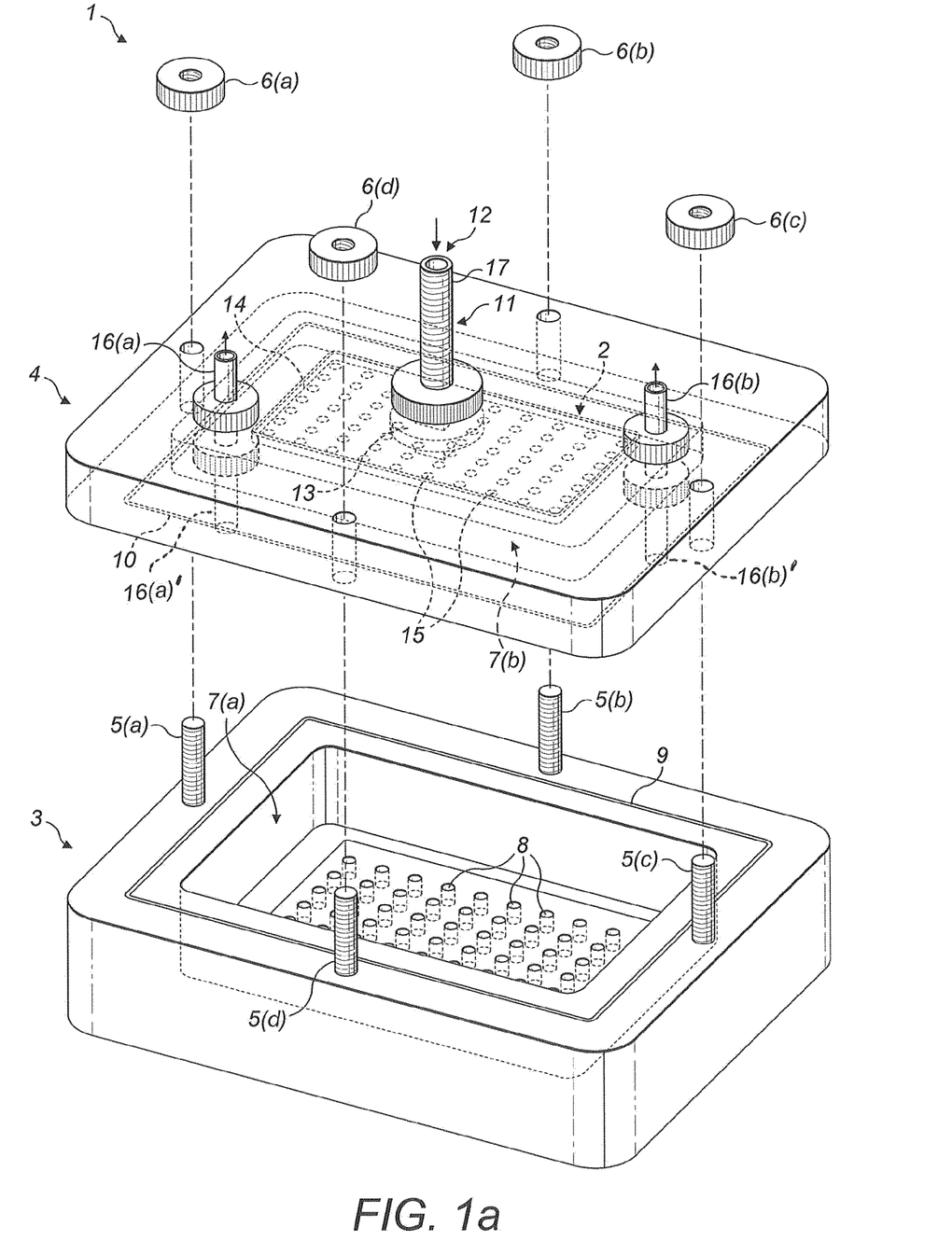
FIG. 1a is an exploded perspective illustration of an exposure device, fluid distribution member and connecting member in accordance with an embodiment of the invention.
Figure 1B:
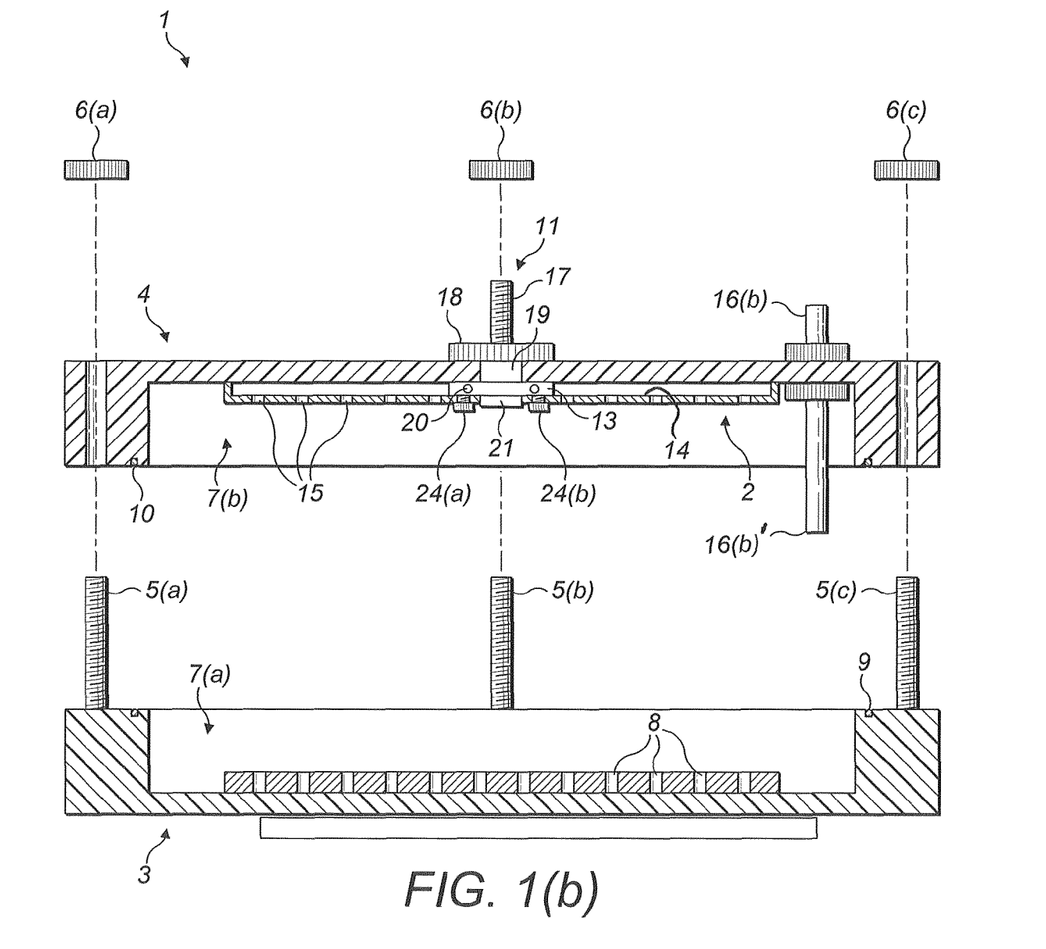
FIG. 1b is an exploded cross sectional illustration of the exposure device, fluid distribution member and connecting member of FIG. 1(a)

Referring to FIGS. 1(a) and 1(b), an exposure device 1, fluid distribution member 2 and connecting member 11 in accordance with an embodiment of the invention are illustrated.

The exposure device 1 includes a base portion 3 and a lid portion 4, manufactured from polymethylmethacrylate (PMMA, Perspex™) which can be connected together using connectors, in this example threaded bolts 5(a) to 5(d) which extend upwardly from a periphery of the base portion 3 and are received through corresponding holes in the lid portion 4 and fastened with manually operated nuts 6(a) to 6(d). In the present example, the exposure device 1 is arranged to expose samples in the form of living cell cultures to a fluid. The base portion 3 and lid portion 4 include respective cavities 7(a), 7(b), which come together to form an exposure chamber 7(a), 7(b) in which a plurality of sample exposure chambers 8, in the illustrated example mounted in a predetermined arrangement within a single unit, may be received and exposed to fluid. The exposure chambers 8 can contain living cell cultures or other samples such as tissue samples to be exposed to a fluid.

Exposure devices such as that illustrated in FIGS. 1(a) and 1(b) are increasingly required to expose larger numbers of sample chambers to fluids, in different chamber arrangements, to increase flexibility, minimise duration and improve efficiency of fluid exposure studies. However, the inventors have observed that it can become difficult to provide substantially uniform fluid to each of the chambers as the number of sample chambers increases.

The fluid distribution member 2, also referred to herein as a conduit, comprises a surface 14 having a plurality of apertures 15 disposed therein for distributing a fluid to the chambers 8 disposed in the exposure chamber 7(a), 7(b). In use, the distribution member 2 receives fluid applied to the surface 14 and distributes the fluid, via the apertures 15, to samples to be exposed to the fluid in the exposure device 1, as will be described in more detail below. This can enable substantially uniform fluid distribution to each of the samples, even with increasing numbers of individual samples to be exposed.

A connecting member 11, also referred to herein as a connector or a manifold, is used to connect the fluid distribution member 2 to the exposure device 1. The connecting member includes a mechanism 21, 24(a), 24(b) for releasably connecting a fluid distribution member 2 to the fluid exposure device 1. In cases in which an exposure device 1 is to be configured to expose a variety of sample arrangements to a fluid, the exposure device 1 can be supplied together with a plurality of fluid distribution members 2, such that these can be individually connected to the fluid exposure device 1 using the connecting member 11, as required.

In the present example, the fluid exposure chamber 7(a), 7(b) is substantially in the shape of a rectangular cuboid. An air-tight seal is provided between the base and lid portions 3, 4. In particular, in the illustrated example, a raised rubber seal 9 is provided on an upper surface of the base portion 3 surrounding the base portion cavity 7(a) and is received within a corresponding groove 10 provided in the lid portion 4 surrounding the lid portion cavity 7(b) when the base and the lid portion 3, 4 are connected, to create an air tight seal between the base and lid portions 3, 4.

Alternatively, the seal can be provided in other ways. For instance, the rubber seal 9 and groove 10 can be interchanged, such that the rubber seal 9 is provided in the lid portion 4 and the groove 10 is provided in the base portion 3. Also, the groove 10 may be omitted, and a raised rubber seal 9 or another seal arrangement, formed in either the base or the lid portion 3, 4, may be brought into contact with a surface of the other of the base or lid portion 3, 4 to create a seal.

As an alternative or in addition to the rubber seal 9 and groove 10, the lid portion 4 may include a lip (not shown) projecting down from the internal rim of the lid cavity 7(b) which, when the lid portion 4 is brought into association with the base portion 3, fits into the top peripheral edge of the base cavity 7(a) and acts as a guide to correctly position the lid portion 4 in relation to the base portion 3. The base portion 3 may alternatively include a lip (not shown) projecting up from the internal rim of the base cavity 7(a) which, when the lid portion 4 is brought into association with the base portion 3, fits into the bottom peripheral edge of the lid cavity 7(b) and acts as a guide to correctly position the lid portion 4 in relation to the base portion 3. Such a lip, whether in the base or lid portion 3,4, may, for instance, include a rubber or other seal, for sealing the base and lid portions 3, 4 together.

In the present example, the connecting member 11 includes a fluid inlet 12 leading to a conduit within the connecting member 11 which extends through the lid portion 4, and which is used to supply fluid, such as smoke, to a fluid distribution outlet unit 13 disposed on the underside of the lid portion 4 between the lid portion 4 and the fluid distribution member 2.

The fluid exits the exposure chamber 7(a), 7(b) via first and second fluid outlets 16(a) and 16(b) disposed at opposite ends of the exposure chamber and separated a distance from the fluid distribution member 2, for instance 2 mm to 20 mm from the edge of the fluid distribution member 2, preferably 5 mm to 10 mm. The first and/or second fluid outlets 16(a), 16(b) may be releasably connected to lid portion 4, for instance with a nut and thread arrangement such as first and second nuts disposed either side of the lid portion 4 engaging with a peripheral thread on the outlets 16(a), 16(b), such that the first and/or second outlets 16(a), 16(b) can be removed for cleaning or replacement with alternative outlets, for instance alternative outlets having different internal conduit cross sections allowing fluid to exit the exposure device 1 at a different rate.

The first and second outlets 16(a), 16(b) each have a shaft 16(a)', 16(b)' extending into the exposure chamber, through the lid portion cavity 7(b) and into the base portion cavity 7(a). In the present example, the shafts 16(a)', 16(b)' extend such that they terminate either side of and below the height of the chambers 8 within the base portion cavity 7(a), and in particular at a position about half of the chamber height from the base of the base portion cavity 7(a).

In use, a plurality of cell culture chambers 8 are populated with cell cultures and placed into the base portion cavity 7(a). The lid portion 4 is connected to the base portion 3 using the connectors 5(a)-(d), 6(a)-(d) so as to form a sealed exposure chamber 7(a), 7(b) having an inlet 12 and first and second outlets 16(a) and 16(b). An exposure fluid, such as cigarette smoke, is supplied to the inlet 12 and travels through the central conduit located within the connecting member 11 to the fluid distribution outlet 13. The fluid distribution member 2 receives the fluid from the fluid distribution outlet 13 and applies the fluid to the surface 14 of the fluid distribution member 2 in which the apertures 15 are formed. The fluid distribution member 2 accordingly distributes the fluid, via the apertures 15, to the cell cultures located within the culture chambers 8 located within the exposure chamber 7(a), 7(b) of the exposure device 1. The fluid is drawn out of the exposure chamber 7(a), 7(b) via the first and second outlets 16(a) and 16(b). Since the shafts 16(a)', 16(b)' of the first and second outlets extend to a position below the height of the chambers 8, fluid is encouraged to take a path via the chambers 8, rather than flowing directly from the inlet 12 to the first and second outlets 16(a), 16(b).

Figure 2:
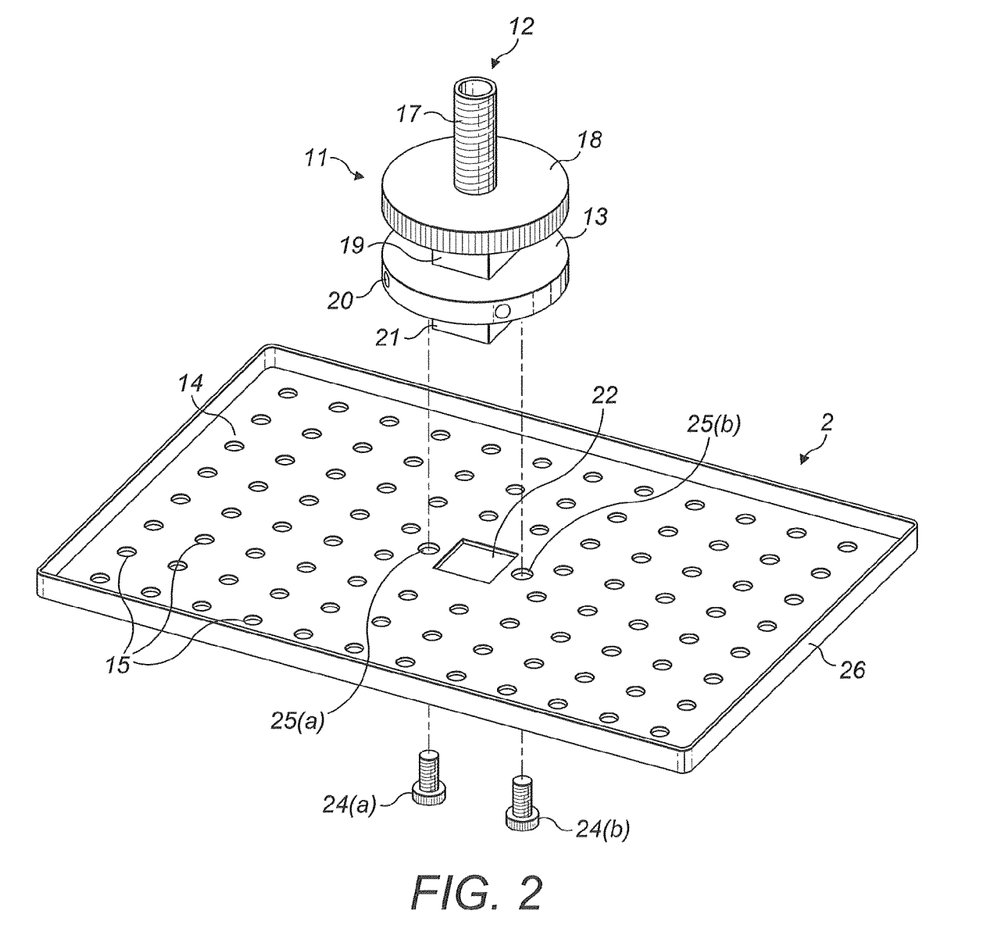
FIG. 2 is an exploded perspective illustration of the fluid distribution member and connecting member of FIGS. 1(a) and 1(b)

FIG. 2 is an exploded perspective illustration of the fluid distribution member 2 and connecting member 11 of FIG. 1.

The connecting member 11, in the illustrated example, comprises the fluid inlet 12 entering the conduit within an externally threaded tubular section 17, on which is screwed a connecting nut 18 for connecting the connecting member 11 to the exposure device 1, in the present example to the lid portion 4 of the exposure device 1. The connecting member 11 may accordingly be releasably connected to the lid portion 4 such that the connecting member 11 can be removed for cleaning or replacement with alternative connectors, for instance alternative connectors having different internal conduit cross sections allowing fluid to enter the exposure device 1 at a different rate.

The threaded tubular section 17 extends into a square cross sectioned shaft 19 which, when the connecting member 11 is connected to the exposure device 1, is arranged to extend through a square hole (not shown) in the lid portion 4. The shaft 19 is connected to the fluid distribution outlet 13, which is formed as a generally cylindrical member, axially aligned with the shaft 19 and of greater diameter than the width of the shaft 19, having a plurality of outlet channels 20, in the present case four such channels, distributed around the outer circumference of the cylinder. The channels 20 lead into a central hub (not shown) within the fluid distribution outlet 13 which in turn leads into the internal conduit extending within the shaft 19 and threaded tubular section 17 connecting the channels 20 to the inlet 12. The channels 20 are spaced symmetrically about the fluid distribution outlet 13 so as to substantially uniformly distribute fluid from the fluid inlet 12 to the upper surface 14 of the fluid distribution member 2.

The connecting member 11 further comprises a fluid distribution member connecting portion for connecting the fluid distribution member 2 to the exposure device 1, in the present example to the lid portion 4 of the exposure device 1. In the present example, the fluid distribution member connecting portion comprises a lug 21 in the form of a projection having a square cross-section, for receiving the fluid distribution member 2 which comprises a corresponding square aperture 22. The lug 21 projects from the under side of the fluid distribution outlet 13, against which the distribution member 2 sits when connected. The lug 21 can be arranged to project a distance from the under side of the fluid distribution outlet 13 corresponding to the thickness of the distribution member 2, such that the base of the lug 21 does not extend below the fluid distribution member 2. First and second distribution member connecting screws 24(a) and 24(b) fasten the fluid distribution member 2 to the connecting member 11, passing through first and second holes 25(a), 25(b) in the distribution member 2 and engaging with threaded bores (not shown) within the fluid distribution outlet 13. The threaded bores are arranged such that they do not coincide with the channels 20 in the fluid distribution outlet 13.

Since the connecting member 11 has a square cross sectioned shaft 19 which is received in a corresponding square hole in the upper wall of the lid portion 4, the connecting member 11 is limited in the number of orientations in which it can be connected to the exposure device 1, in the present case four orientations. Since the connecting member 11 is symmetrical in two planes, the specific one of these four orientations which is chosen will not influence the operation of the connecting member 11. Accordingly, the connecting member 11, and therefore components of the member 11 such as the outlets 20, can be accurately oriented with respect to the exposure device 1, and as the connecting nut 18 for connecting the connecting member 11 to the exposure device 1 is tightened, the connecting member 11 is prevented from rotating in relation to the exposure device 1.

The lug 21 of the connecting member 11 also has a square cross section which is received in a corresponding square hole 22 in the fluid distribution member 2. The fluid distribution member 2 is therefore limited in the number of orientations in which it can be connected to the connecting member 11, in the present case to four orientations. Accordingly, the fluid distribution member 2 can be accurately oriented with respect to the connecting member 11 and accordingly with respect to the exposure device 1.

The fluid distribution member 2 is formed as a substantially flat plate having a raised wall 26 at its peripheral edge which, in use, contacts a surface of the exposure device 1. In particular, in the present example, when the fluid distribution member 2 is fitted to the exposure device 1, the wall 26 is brought into contact with the flat inside surface of the lid portion 4 of the exposure device 1, and a chamber is formed between the flat inside surface of the lid portion 4, the peripheral wall 26 of the fluid distribution member 2 and the upper surface 14 of the fluid distribution member 2. In use, exposure fluid enters this chamber and disperses throughout the chamber prior to passing through the apertures 15 as previously described.

The exposure device 1 is arranged to accommodate multiple cell culture chambers 8, for instance in pre-existing arrangements, such as a Microtitre plate (also referred to as a microplate or microwell plate), which is a flat plate with multiple chambers, also referred to as wells. Such a plate may have 6, 12, 24, 48, 54, 96, 384 or 1536 sample wells arranged in a 2:3 or 3:4 rectangular matrix, for instance 2 rows and 3 columns of wells, 4 rows and 6 columns of wells, 8 rows and 12 columns of wells etc. The use of such sample plates, for instance the 96-well plate, facilitates the analysis of the samples with an automated plate reader such as the Cellomics ArrayScan VTI HCS Reader. Fluid distribution member 2 illustrated in FIG. 2 is configured for use with the chambers 8. In the present example, the fluid distribution member 2 has a similar shape and size to the topography of the chambers 8, in particular being generally rectangular in shape. The fluid distribution member 2 also includes apertures which correspond to individual chambers 8 or groups of chambers 8. For instance, in the illustrated example, the apertures 15 are individually arranged to correspond to single wells of a 96-well plate, and accordingly, in use, to distribute fluid to such wells uniformly.

The exposure device 1 is also arranged such that fluid distribution members 2 can be interchanged, and accordingly such that other fluid distribution member aperture arrangements can be readily used, by disconnecting a fluid distribution member 2 connected to the exposure device 1 using the connecting member 11 and connecting an alternative distribution member using the connecting member 11. It will therefore be understood that distribution members which have been optimised for particular arrangements of samples and/or types of matter or fluid to be exposed in the exposure device 1 can be selectively connected to the exposure device 1. As an example, arrangements of cell culture chambers which are non-symmetrical, or only symmetrical in 2 planes, such as those illustrated in FIGS. 1(*a*) and (*b*), require corresponding fluid distribution members and these can be selected on that basis.

Although the fluid distribution member 2 illustrated in FIGS. 1(*a*), 1(*b*) and 2 comprises apertures corresponding to wells or chambers within a 96-well plate and arranged to expose smoke to cell cultures within the wells, distribution members can alternatively be used which have apertures corresponding to and used to distribute smoke or other fluids substantially uniformly to other well or chamber arrangements such as arrangements having 6, 12, 24, 48, 96, 384 or 1536 sample wells, and/or containing other samples such as mammalian lung, skin and/or oral cell cultures, human or rodent whole lung slices, saliva, and/or prokaryotes (bacterial cells for genotoxicity testing). Other suitable samples would be apparent to those skilled in the art. One particular example is the exposure of lung epithelial cells to cigarette smoke in a 96-well format.

FIGS. 3(*a*) to 3(*d*) illustrate fluid distribution members according to embodiments of the invention, designed for use within an exposure device housing a 96-well plate, as illustrated in FIGS. 1(*a*), 1(*b*) and 2.

In FIG. 3(*a*), a fluid distribution member 30, manufactured from a 1 mm thick plate of stainless steel, comprises an arrangement of 2.5 mm diameter circular apertures 31 spaced apart such that approximately one aperture corresponds to every other well of a 96-well plate. In particular, whereas a 96 well plate can include wells arranged in a 12 by 8 format with 12 columns of wells and 8 rows, the apertures in the fluid distribution member 30 of FIG. 3(*a*) are arranged in a 12 by 4 format, with 12 columns of apertures 32 each having 4 apertures offset from immediately neighbouring columns by half the space between apertures in the column, such that substantially every other well of a 96 well plate has a corresponding aperture. At the centre of the distribution member 30, is provided a square aperture 33 for connecting the distribution member 30 to an exposure device 1 using a connecting member such as that illustrated in FIGS. 1(*a*), 1(*b*) and 2. In the region of this square connecting aperture 33, a number of apertures, two in this case, are omitted. Such apertures coincide with the square aperture 33, or would otherwise be close to the outlet channels 20 in the connecting member 11, potentially resulting in a non-uniform fluid distribution if they were located in such a position.

In FIG. 3(*b*), a fluid distribution member 40, manufactured from a 1 mm thick plate of stainless steel, comprises an arrangement of 2.5 mm diameter circular apertures 41 spaced apart such that approximately one aperture corresponds to each well of a 96-well plate. In particular, the apertures in the fluid distribution member 40 of FIG. 3(*b*) are arranged in a 12 by 8 format, with 12 columns of apertures 42 each having 8 apertures aligned with the apertures of neighbouring columns, such that substantially every well of a 96 well plate has a corresponding aperture. Similarly to the member 30 of FIG. 3(*a*), at the centre of the distribution member 40 a square aperture 43 for connecting the distribution member 40 to an exposure device using a connecting member such as that illustrated in FIGS. 1(*a*), 1(*b*) and 2 is provided. A number of apertures, four in this case, are omitted from this region for the reasons mentioned above.

In FIG. 3(*c*), a fluid distribution member 50, manufactured from a 1 mm thick plate of stainless steel, comprises an arrangement of 2.0 mm wide by 60 mm slotted, substantially rectangular apertures 51 spaced apart such that approximately one aperture corresponds to each column of wells in a 96-well plate. In particular, the apertures in the fluid distribution member 50 of FIG. 3(*c*) are arranged in a 12 slot format, with the 12 slots running parallel to each other and corresponding to columns of wells in a 96 well plate. Similarly to the members 30 and 40 of FIGS. 3(*a*) and 3(*b*), at the centre of the distribution member 50, a square aperture 53 for connecting the distribution member 50 to an exposure device using a connecting member such as that illustrated in FIGS. 1(*a*), 1(*b*) and 2, is provided. There is a break in the length of the slots, resulting in two sets of two slots arranged either side of the square aperture 53, in this region for the reasons mentioned above.

In FIG. 3(*d*), a fluid distribution member 60, manufactured from a 1 mm thick plate of stainless steel, comprises an arrangement of 8.0 mm diameter circular apertures 61 spaced apart such that approximately one aperture corresponds to each well of a 96-well plate. In particular, the apertures in the fluid distribution member 60 of FIG. 3(*d*) are arranged in a 12 by 8 format, with 12 columns of apertures 62 each having 8 apertures aligned with the apertures of neighbouring columns, such that substantially every well of a 96 well plate has a corresponding aperture. Similarly to the members 30, 40 and 50 of FIGS. 3(*a*)-(*c*), at the centre of the distribution member 60, a square aperture 63 for connecting the distribution member 60 to an exposure device using a connecting member such as that illustrated in FIGS. 1(*a*), 1(*b*) and 2, is provided. A number of apertures, four in this case, are omitted from this region for the reasons mentioned above.

Advantageous features have been described above in relation to specific embodiments of the exposure device, fluid distribution member and connecting member, having specific implementations. However, the present disclosure is not limited to such specific embodiments.

For example, although the exposure device 1 has been described as being arranged to accommodate cell culture chambers, other containers to be exposed to fluids can be used in the present exposure devices.

Also, the exposure device 1 has been described as one which, in use, only has inlets and outlets for the exposure fluid. However, the device can also be adapted to include an inlet and an outlet for nutrient media used to support cell cultures in culture chambers within the device. There are, for instance, 96-well and other plates commercially available containing a porous membrane support which would allow nutrient supply via liquid cell culture medium into the chamber, during exposure to smoke. Corning HTS Transwell-96 Permeable Support Plates for Cell Migration, as supplied by Fisher Scientific, are an example of such plates. The device can be adapted to accommodate nutrient media, for instance, in accordance with the device described in International Patent Publication No. WO03/100417, the entirety of which is hereby expressly incorporated by reference.

Although the exposure device 1 as been described as being manufactured from Perspex™ and the distribution plates from stainless steel, other materials can be used for either or both of these components, such as stainless steel, glass, PTFE, Perspex™ etc.

Exposure devices as described herein have the advantage that the distribution plate can be quickly and easily replaced according to the requirements of exposure concerned. A particular connection device has been described for achieving this, having a shaft with a square cross section for extending through a portion of the exposure device and a lug with a square cross section onto which the distribution plates can be screwed. Using a non-circular shaped shaft and lug, mating with corresponding square apertures in the exposure device and distribution plate, enables the connecting member and distribution plate to be easily aligned in the correct manner with the exposure device. However, other arrangements can be used, such as other shapes of shaft and/or lug to achieve the desired advantages or other connecting mechanisms, such as other screw arrangements, latches etc.

Furthermore, the connecting member has been described as a removable component from the exposure device, as well as having a fluid conduit extending therethrough, for instance allowing alternative connection members to be used with different diameters of fluid conduit, or arranged to receive different smoke distribution members based on the shape of the connecting lug or equivalent arrangement. However, the connecting member can alternatively be provided as a permanent component of a distribution plate and/or or exposure device. Also, the fluid inlet need not be provided as a part of the connecting member and/or the exposure device can contain a permanent, non-replaceable fluid distribution member.

The fluid used in the exposure device can comprise any fluid which it may be desirable to expose samples to and which is compatible with the materials from which the exposure device and related components are manufactured. For instance, the fluid may be combustion smoke, for instance cigarette smoke as described above, air, exhaust gases, single gases or mixtures of gases, cosmetic and pharmaceutical aerosols, other aerosolised consumer goods such as cleaning products, pesticides, herbicides and engineered nanoparticles (permitting there is a generator for such aerosols) etc.

Although the fluid distribution members illustrated in FIGS. 3(a) to 3(d) comprise apertures corresponding to wells or chambers within a 96-well plate and arranged to expose smoke to cell cultures within the wells, distribution members can alternatively be used which have apertures corresponding to and used to distribute smoke or other fluids substantially uniformly to other well or chamber arrangements such as arrangements having 6, 12, 24, 48, 96, 384 or 1536 sample wells. For example, the slotted distribution plate 50 of FIG. 3(c) may include between 2 and 30 slots or sets of one or more slots, for instance 2, 3, 4, 6, 8, 10, 12, 15, 16, 18, 20, 24, 28, or 30 slots or sets of one or more slots. The number of slots may be determined based on the number of rows or columns of chambers or wells used in a sample plate.

Example

A fluid exposure device was used to test the viability of cells exposed to cigarette smoke, to determine the uniformity of smoke distribution when distribution members as described herein with reference to FIGS. 3(a) to 3(d) were fitted into the device.

Human pulmonary adenocarcinoma cells (H292) were seeded at a density of $2 \times 10^5$ cells/ml (cell passages 85-100) into the central 60 wells of a number of 96 well plates (leaving a border of 36 wells blank as per standard procedure). Each of the 96 well plates was inserted into an exposure chamber of an exposure device, fitted with a respective one of the four fluid distribution members described with reference to FIGS. 3(a) to 3(d). A Borgwaldt RM20S smoking machine was used to generate smoke at the ISO regime, using 10 mg 3R4F reference cigarettes. Cells were exposed for 30 minutes at the air-plastic interface (API), and each fluid distribution member was tested with a minimum of two smoke dilutions, in particular a cigarette smoke and air mixture in a 1:25 smoke:air volume ratio and a cigarette smoke and air mixture in a 1:50 smoke:air volume ratio.

Cell viability of exposed cells was assessed using a commercially available assay, Cell Titer-Glo assay, following the standard procedure.

Figure 3A:
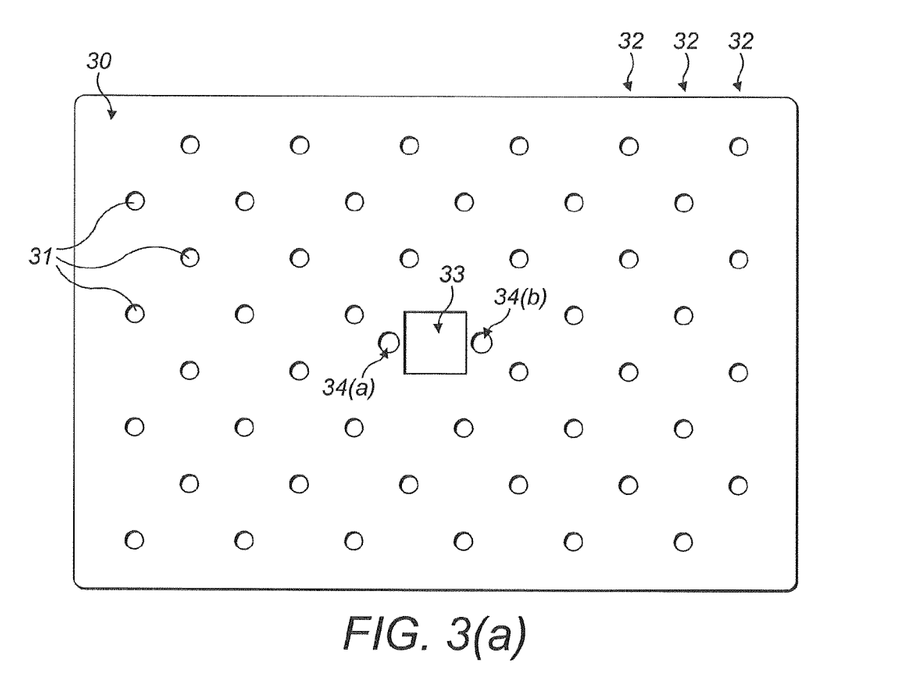
FIGS. 3(a) to 3(d) are plan illustrations of respective fluid distribution members according to respective embodiments of the invention.
Figure 3B:
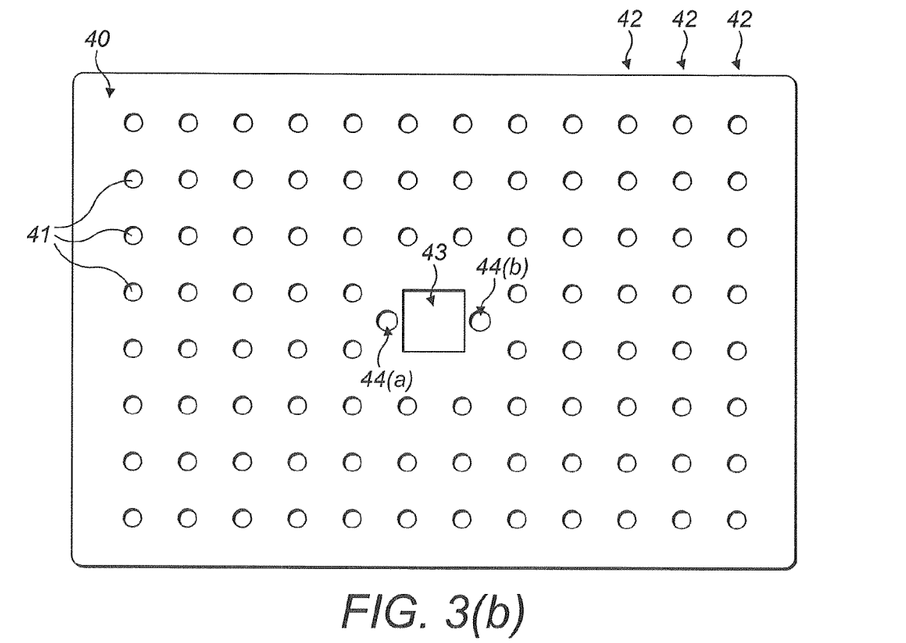
Figure 3C:
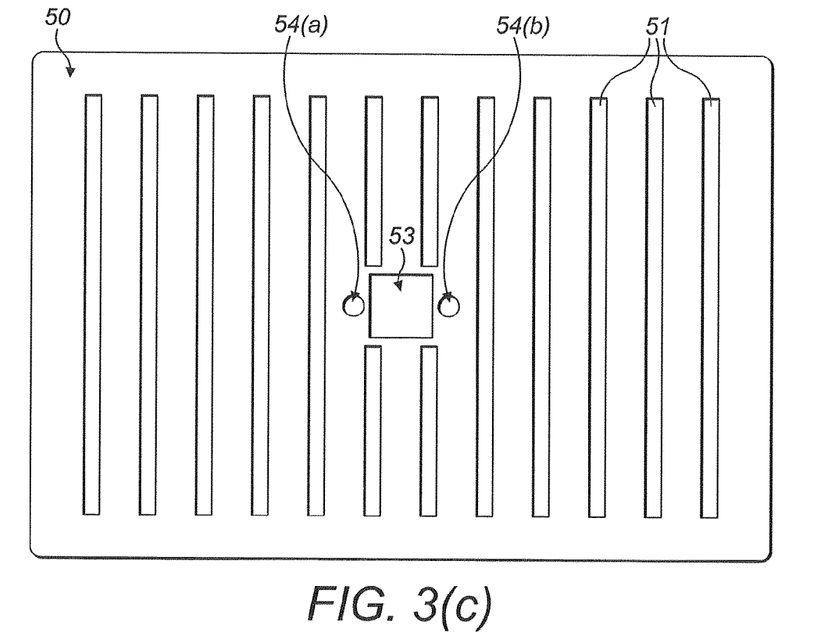
Figure 3D:
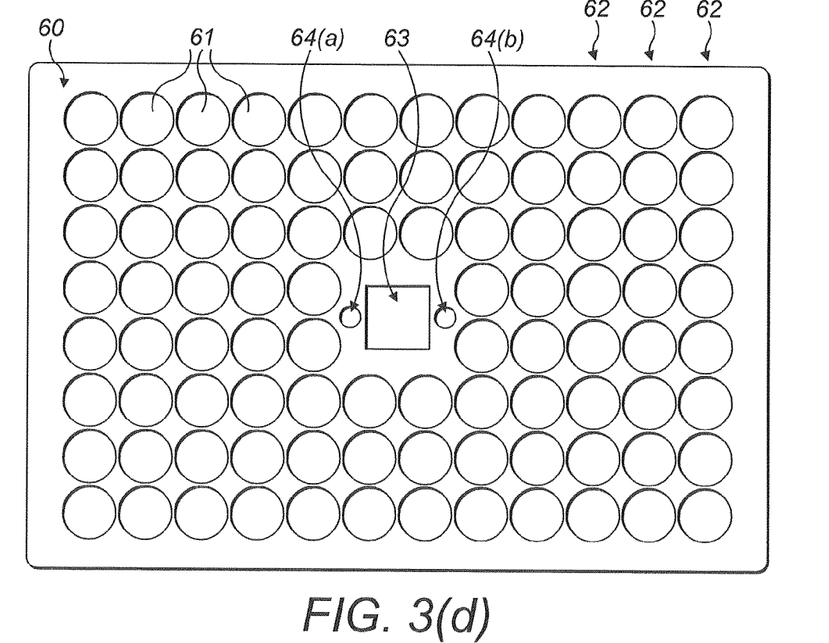
Figure 4:
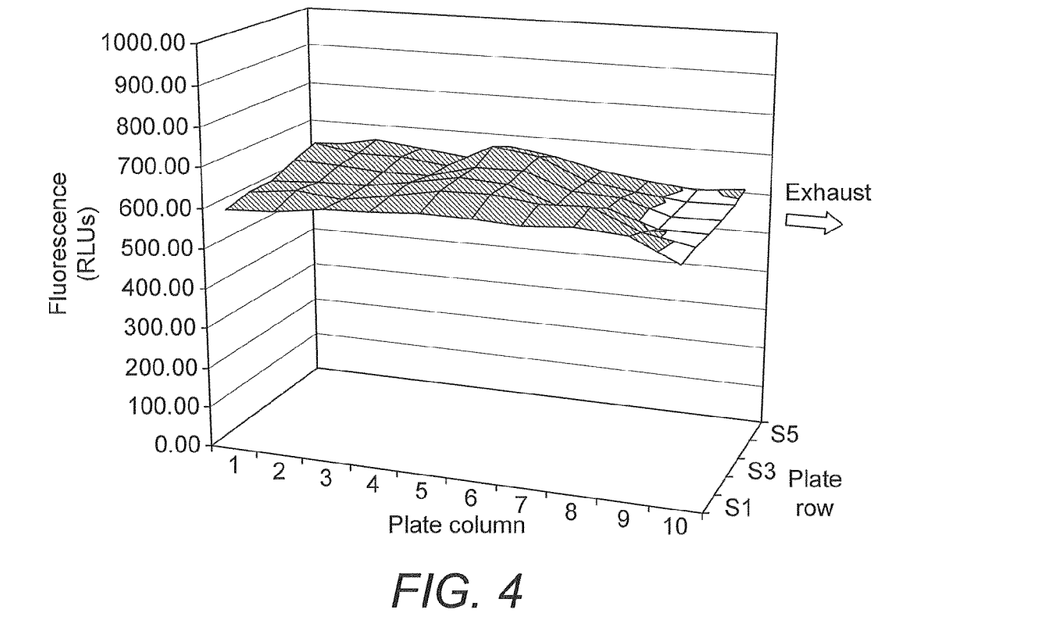
FIG. 4 is a graph illustrating the viability, based on the cytotoxicity assay Cell Titer-Glo (CTG), of cells present in 60 wells of a 96-well plate when exposed to cigarette smoke and air for 30 minutes in a 1:250 smoke:air volume ratio which was distributed across the wells via a slotted fluid distribution member according to an embodiment of the invention.
Figure 5:
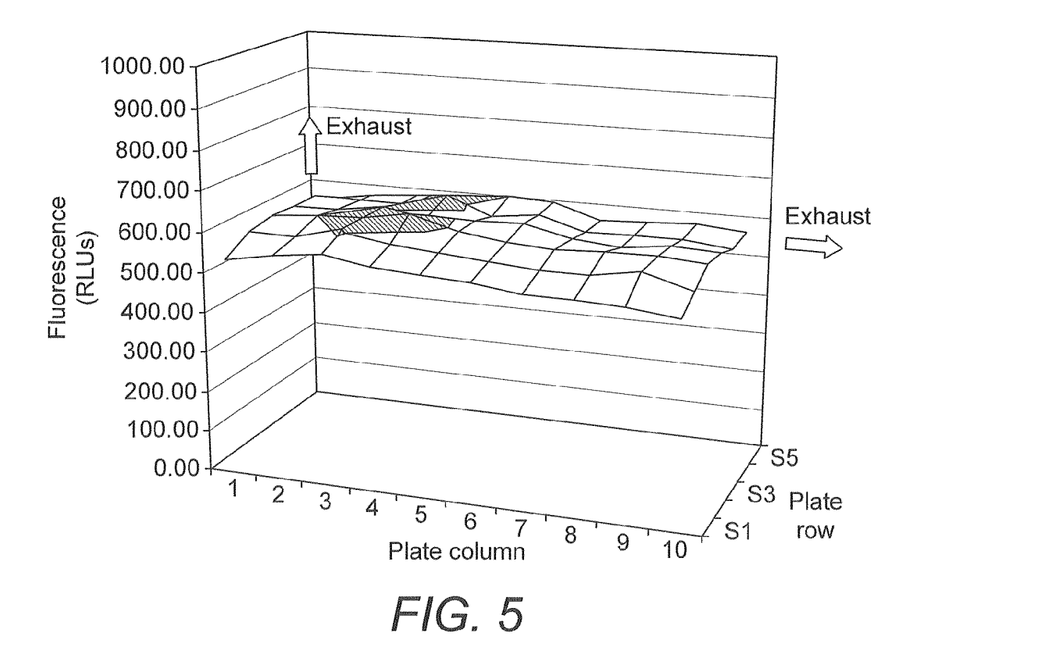
FIG. 5 is a graph illustrating viability, based on the cytotoxicity assay called Cell Titer-Glo (CTG), of cells present in 60 wells of a 96-well plate when exposed to cigarette smoke and air for 30 minutes in a 1:50 smoke:air volume ratio which was distributed across the wells via a slotted fluid distribution member according to an embodiment of the invention.
Figure 6:
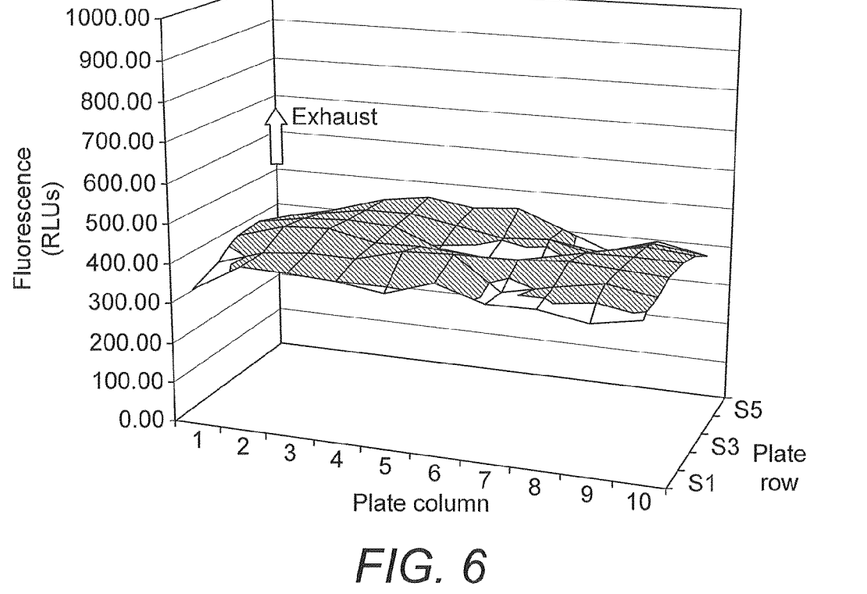
FIG. 6 is a graph illustrating the viability, based on the cytotoxicity assay Cell Titer-Glo (CTG), of cells present in 60 wells of a 96-well plate when exposed to cigarette smoke and air for 30 minutes in a 1:25 smoke:air volume ratio which was distributed across the wells via a slotted fluid distribution member according to an embodiment of the invention.
Figure 7:
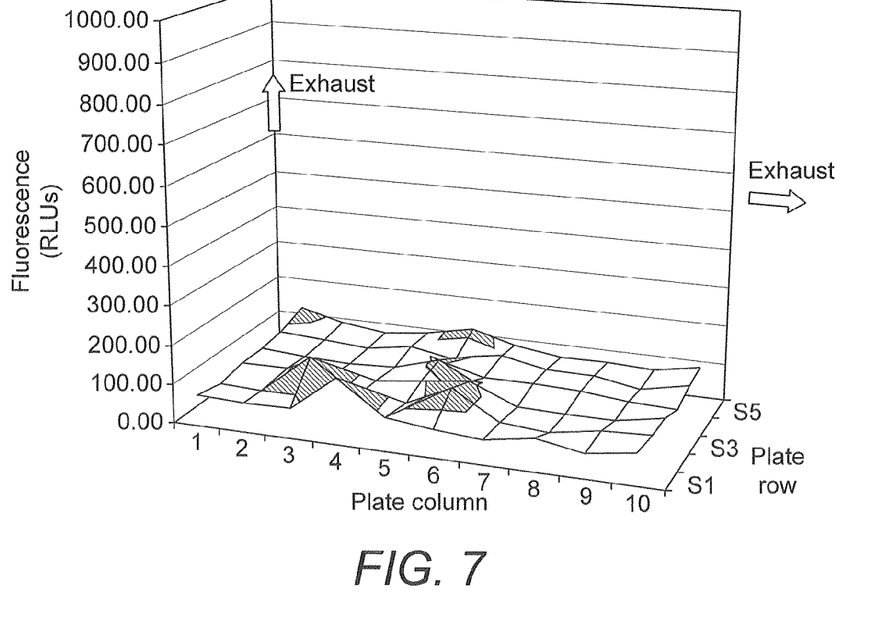
FIG. 7 is a graph illustrating the viability, based on the cytotoxicity assay Cell Titer-Glo (CTG), of cells present in 60 wells of a 96-well plate when exposed to cigarette smoke and air for 30 minutes in a 1:10 smoke:air volume ratio which was distributed across the wells via a slotted fluid distribution member according to an embodiment of the invention.

The results indicate that the slotted fluid distribution plate illustrated in FIG. 3(c) gave the most uniform smoke distribution of the four plates on test. This plate was also tested with a cigarette smoke and air mixture in a 1:250 smoke:air volume ratio and a cigarette smoke and air mixture in a 1:10 smoke:air volume ratio. The surface contours of cell viability within the slotted plate when tested with a 1:250, 1:50, 1:25 and 1:10 smoke:air volume ratio are respectively presented in 2 dimensions in FIGS. 4 to 7. As can be seen from these graphs, substantially uniform cell viability was observed when the slotted distribution plate of FIG. 3(c) was used, across the broad range of smoke dilutions.

In order to address various issues and advance the art, the entirety of this disclosure shows by way of illustration various embodiments in which the claimed invention(s) may be practiced and provide for superior techniques for fluid distribution and fluid exposure in a fluid exposure device. The advantages and features of the disclosure are of a representative sample of embodiments only, and are not exhaustive and/or exclusive. They are presented only to assist in understanding and teach the claimed principles. It should be understood that they are not representative of all claimed inventions. As such, certain aspects of the disclosure have not been discussed herein. That alternate embodiments may not have been presented for a specific portion of the invention or that further undescribed alternate embodiments may be available for a portion is not to be considered a disclaimer of those alternate embodiments. It will be appreciated that many of those undescribed embodiments incorporate the same principles of the invention and others are equivalent. Thus, it is to be understood that other embodiments may be utilized and modifications may be made without departing from the scope and/or spirit of the disclosure. As such, all examples, implementations, and/or embodiments are deemed to be non-limiting throughout this disclosure. Also, no inference should be drawn regarding those embodiments discussed herein relative to those not discussed herein other than it is as such for purposes of reducing space and repetition. Various embodiments may suitably comprise, consist of, or consist essentially of, various combinations of the disclosed elements, components, features, parts, steps, means, etc. Some of the disclosed features, elements, implementation, etc., may be mutually contradictory, in that they cannot be simultaneously present in a single embodiment. Similarly, some features are applicable to one aspect of the disclosure, and inapplicable to others. In addition, the disclosure includes other inventions not presently claimed. Applicant reserves all rights in those presently unclaimed inventions including the right to claim such inventions, file additional applications, continuations, continuations in part, divisions, and/or the like thereof. As such, it should be understood that advantages, embodiments, examples, functional, features, structural, and/or other aspects of the disclosure are not to be considered limitations on the disclosure as defined by the claims or limitations on equivalents to the claims.

The invention claimed is:

1. A fluid exposure kit comprising:

a fluid exposure device for exposing samples to a fluid, the device comprising a plurality of sample chambers;

a plurality of fluid distribution members, each including:

a plurality of apertures in a surface thereof and configured such that, in use, when a fluid distribution member of the plurality of fluid distribution members is fitted to the fluid exposure device, said fluid distribution member receives a fluid applied to a surface thereof and distributes the fluid, via the plurality of apertures, to samples in the fluid exposure device; and a fluid exposure device connection part; and a connecting member configured to releasably connect with the fluid exposure device connection part of a fluid distribution member of the plurality of fluid distribution members to releasably connect said fluid distribution member to the fluid exposure device, the connecting member configured to releasably connect an individual one of the plurality of fluid distribution members interchangeably to the fluid exposure device, and wherein all of the plurality of apertures of one of the fluid distribution members together form first arrangement and all of the plurality of apertures of another one of the fluid distribution members together form a second arrangement that is different to the first arrangement, such that, in use, a particular fluid distribution member can be selected from the plurality of fluid distribution members according to an arrangement of samples to be exposed in the fluid exposure device, wherein the plurality of apertures of the first arrangement and the plurality of apertures of the second arrangement differ in at least one of size, shape, position, or number, the plurality of apertures of at least one of the fluid distribution members defining a plurality of elongate slots extending in parallel across said fluid distribution member, at least one of the elongate slots extending a distance greater than half of a width of said fluid distribution member, each said plurality of apertures configured to correspond with a plurality of sample chambers within the fluid exposure device, so as to distribute the fluid to each of the plurality of sample chambers in the fluid exposure device, and the fluid exposure device comprising a material that is compatible with the fluid, the fluid including at least one of: a single gas, a mixture of gases, combustion smoke, cigarette smoke, air, an exhaust gas, a cosmetic aerosol, a pharmaceutical aerosol, an aerosolized consumer good, a pesticide, an herbicide, and engineered nanoparticles.

2. The fluid exposure kit according to claim 1, wherein the slots are configured to correspond with an arrangement of samples to be exposed to the fluid in the fluid exposure device.

3. The fluid exposure kit according to claim 2, wherein the arrangement of samples comprises an arrangement has a microtiter well format.

4. The fluid exposure kit according to claim 1, wherein the plurality of apertures includes between 2 and 30 slots or sets of one or more slots.

5. The fluid exposure kit according to claim 1, wherein the fluid exposure device includes a side wall that is substantially perpendicular to a surface thereof and circumscribes the surface.

6. The fluid exposure kit according to claim 1, wherein the fluid exposure device connection part is configured to connect a fluid distribution member of the plurality of fluid distribution members to the fluid exposure device in a limited number of orientations.

7. The fluid exposure kit according to claim 1, wherein the connecting member comprises:

an inlet configured to receive fluid to be distributed by a fluid distribution member of the plurality of fluid distribution members; and at least one channel configured to supply the fluid from the inlet to a surface of said fluid distribution member.

8. The fluid exposure kit according to a claim 1, wherein the fluid exposure device defines a cavity configured to receive a plurality of sample chambers, the fluid exposure device configured to provide substantially contemporaneous and uniform fluid exposure to each of the sample chambers.

9. A method of exposing samples to the fluid in the fluid exposure device of the fluid exposure kit according to claim 1, the method comprising:

providing the fluid to the surface of one of the plurality of fluid distribution members such that the fluid is distributed, via the plurality of apertures in the surface of said one of the plurality of fluid distribution members, to samples in the fluid exposure device;

selecting said one of the plurality of fluid distribution members according to an arrangement of samples to be exposed in the fluid exposure device; and connecting said one of the plurality of fluid distribution members to the fluid exposure device using the connecting member.

* * * * *